United States Patent

Imazato et al.

[11] Patent Number: 5,408,022
[45] Date of Patent: Apr. 18, 1995

[54] ANTIMICROBIAL POLYMERIZABLE COMPOSITION, THE POLYMER AND ARTICLE OBTAINED FROM THE SAME

[75] Inventors: Satoshi Imazato; Mitsuo Torii, both of Suita; Yasuhiko Tsuchitani, Nara; Koji Nishida; Junichi Yamauchi, both of Kurashiki, all of Japan

[73] Assignee: Kuraray Co., Ltd., Kurashiki, Japan

[21] Appl. No.: 962,736

[22] Filed: Oct. 19, 1992

[30] Foreign Application Priority Data

Oct. 18, 1991 [JP] Japan .................................. 3-299958

[51] Int. Cl.⁶ .......................................... C08F 226/06
[52] U.S. Cl. .................................... 526/259; 526/265
[58] Field of Search ................ 560/205; 526/258, 259, 526/265

[56] References Cited

FOREIGN PATENT DOCUMENTS 2253774  5/1973  Germany .

OTHER PUBLICATIONS

E. Prokopova and J. Stejskal, Journal of Polymer Science; Polymer Physics Edition 12, 1537–1546 (1974).

*Primary Examiner*—Joseph L. Schofer
*Assistant Examiner*—Wu C. Cheng
*Attorney, Agent, or Firm*—Oblon, Spivak, McClelland, Maier & Neustadt

[57] ABSTRACT

An antimicrobial polymerizable composition comprising an ethylenically unsaturated monomer, a specific monomer having antimicrobial activity and a polymerization initiator. The composition gives, upon polymerization, a polymer having permanent antimicrobial activity, which is very useful for medical articles, in particular dental materials.

1 Claim, No Drawings

ANTIMICROBIAL POLYMERIZABLE COMPOSITION, THE POLYMER AND ARTICLE OBTAINED FROM THE SAME

BACKGROUND OF THE INVENTION

1. Field of the Invention

The present invention relates to a polymerizable composition that can yield an unreleasable antimicrobial polymer and, more specifically, to a polymerizable composition capable of yielding an unreleasable antimicrobial polymer from which the antimicrobial component is not released, and the polymer and medical articles obtained from the composition.

The medical articles produced according to the present invention includes artificial blood vessels, artificial skin, wound-covering materials, catheters, sutures, dental materials (adhesives, coating agents, composite resins and the like), contact lens, bone cement and the like.

2. Description of the Prior Art

Polymers having antimicrobial properties are known. For example, polymers containing a releasable antimicrobial component have this property. It has been considered necessary that an antimicrobial component be entrapped by bacteria or enclosed by then to be effective and kill or inactivate them. For this purpose, it has been considered necessary that the antimicrobial component elute, i.e. be released, from the polymer to contact the bacteria without restriction. For example, "Synthesis and Antibacterial Activities of Copolymers Having a Quaternary Salt Group", on pages 934–939 of METAL, INORGANIC AND POLYMER MATERIALS, the 9th series, which discloses research and development issued from the Agency of Industrial Science and Technology, reports that an acrylonitrile copolymer containing ammonium chloride groups is released to develop an antimicrobial property against *Bacillus subtilis* or *Staphylococcus aureus*. Japanese Patent Application Laid-open No. 201806/1987 discloses an antimicrobial dental composition containing cetylpyridinium chloride that is a known cationic surfactant.

By releasing the anitimicrobial component, however, the antimicrobial activity decreases over time and is lost when the active component is gone. Antimicrobial components often give hazardous action to normal tissue and after, having been released, they migrate also to normal tissue, whereby it is impossible to prevent the hazardous action completely. Incorporation of antimicrobial agents often causes the matrix to decrease its mechanical properties.

The antimicrobial activity in the field of dental materials is briefly described below. Caries, which is a representative dental disease, develops by dissolution of enamel with acids produced by bacteria in the oral cavity. Streptococcus mutans is an important bacterium causing caries. Periodontitis, which is a disease of periodontal tissue, also develops by bacteria present in the oral cavity. It is important for preventing either of these diseases to prevent the bacteria from forming plaque on the surface of dentin or to remove the plaque quickly once formed. Regular toothbrushing is recommended to these ends.

Where a dental prosthesis has been used to fill or restore a caries with a dental material such as a resin or composite resin, it is also important, for the purpose of preventing the development of secondary caries or periodontitis, to remove plaque that readily forms on the surface of the material caused by adhesion of bacteria.

To prevent caries, a known practice is the topical application of fluoride, i.e. application to dentin of an acid phosphoric fluoride (APF) solution or a diamine silver fluoride solution, which improves the acid resistance of enamel. Several attempts have also been made, while paying attention to the dental material used, to prevent plaque from depositing on, the material. Thus, incorporation of antimicrobial agents in dental materials has been attempted, and there have been reported, for example, a composite resin incorporating chlorohexidine (K. Takemura et al, The Japanese Journal of Conservative Dentistry, Vol. 26, (2), 540–547, 1983), calcium phosphate-based cement incorporating metronidazole (M. Iwaku et al, The Japanese Journal of Conservative Dentistry, Vol. 30, (5), 1444–1448, 1987).

Such simple incorporation of an antimicrobial agent in dental material, however, cannot assure satisfactorily durable antimicrobial activity, since the agent is entirely released in a short period of time. The incorporation further has the problem of decreasing the mechanical properties of the matrix material.

Furthermore, releasing of an antimicrobial agent contained in a dental composition may, while influencing the surface of the composition, badly influence bacterial flora surrounding the composition in the oral cavity.

SUMMARY OF THE INVENTION

Accordingly, an object of the present invention is to provide an antimicrobial dental composition that does not allow its antimicrobial component to be released out.

Thus, the present invention provides a polymerizable composition comprising an ethylenically unsaturated monomer, at least one mono-, di- or trifunctional monomer selected from the group represented by the following general formulas I through III and having antimicrobial activities and a polymerization initiator

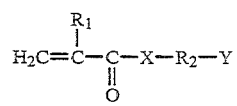

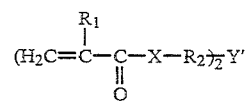

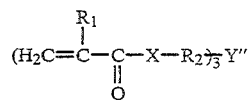

wherein $R_1$ represents a hydrogen atom or a methyl group, $R_2$ represents an alkylene group having 2 to 18 carbon atoms, X represents an oxygen atom, a sulfur atom or an imide group and Y, Y' and Y" represent any one selected from the following respective formulas:

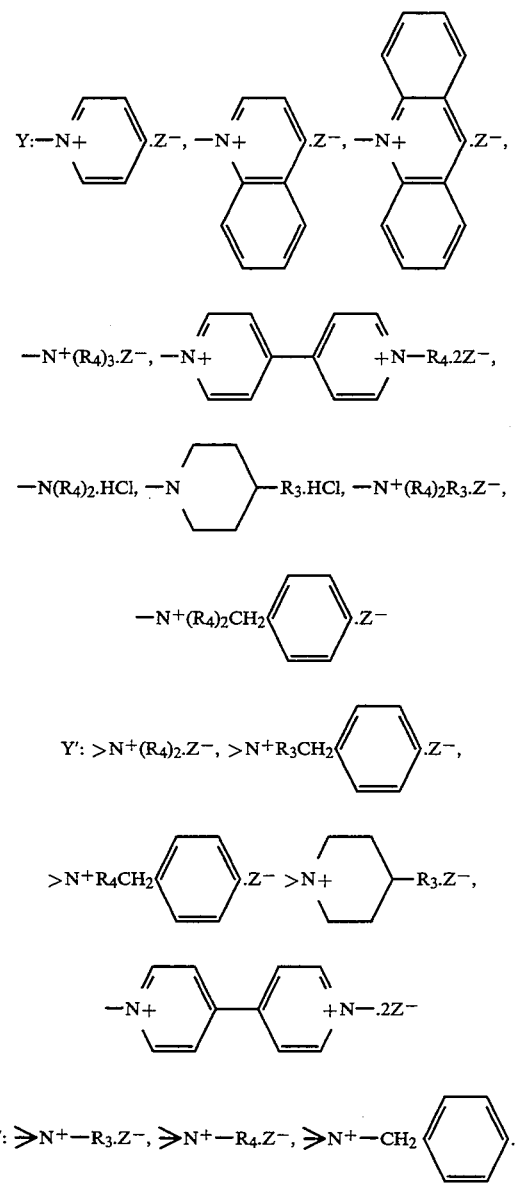

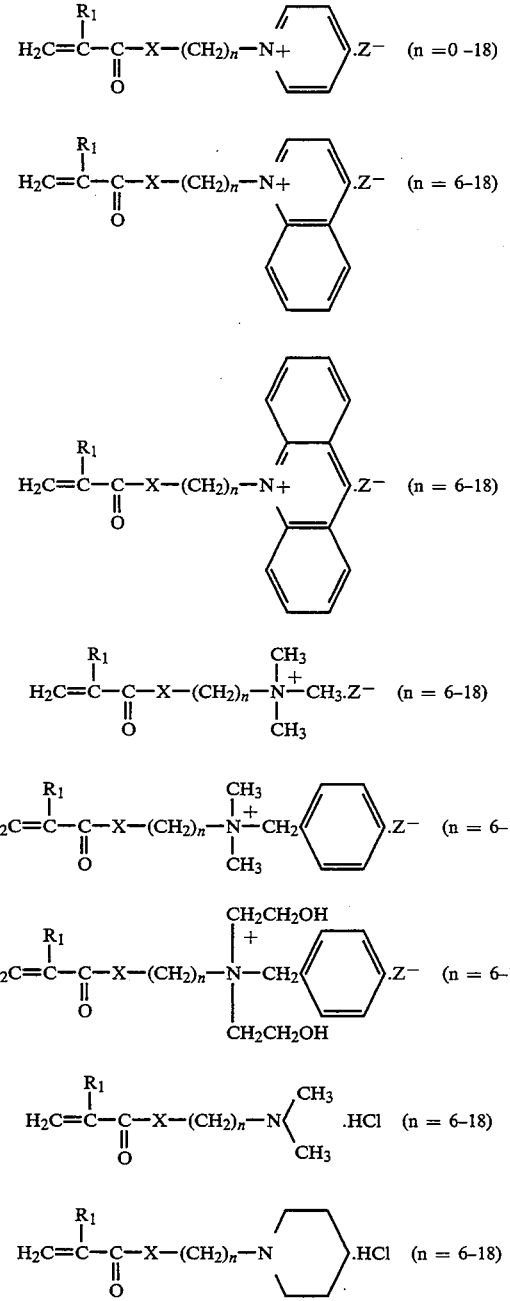

wherein $R_3$ represents a hydrogen atom or an alkyl group having 1 to 18 carbon atoms, $R_4$ represents a methyl group, a ethyl group or a hydroxyethyl group and Z represents a chlorine atom or bromine atom.

The present invention further provides an antimicrobial linear copolymer obtained by polymerizing a monofunctional ethylenically unsaturated monomer and a monofunctional antimicrobial monomer represented by the above general formula I, in the presence of a polymerization initiator. The present invention also provides an antimicrobial crosslinked copolymer obtained by polymerizing a mono- or multifunctional ethylenically unsaturated monomer and an antimicrobial monomer represented by the above formula I, II or III, in the presence of a polymerization initiator.

The present invention still further provides an unreleasable antimicrobial medical article obtained by shaping the above linear polymer and, also, an unreleasable antimicrobial medical article obtained by shaping the above crosslinked polymer.

DETAILED DESCRIPTION OF THE PREFERRED EMBODIMENTS

The polymer obtained from the composition of the present invention has antimicrobially active regions, which do not dissociate from the polymer. The antimicrobial activities developed by the structure of the polymer of the present invention cannot be explained by conventional concepts. It is, however, considered to be due to some action exerted by the antimicrobial regions against bacteria that have come into contact with the polymer thus killing or inactivating them.

Specific examples of the antimicrobial compound used in the invention are as follows.

Compounds represented by formula I

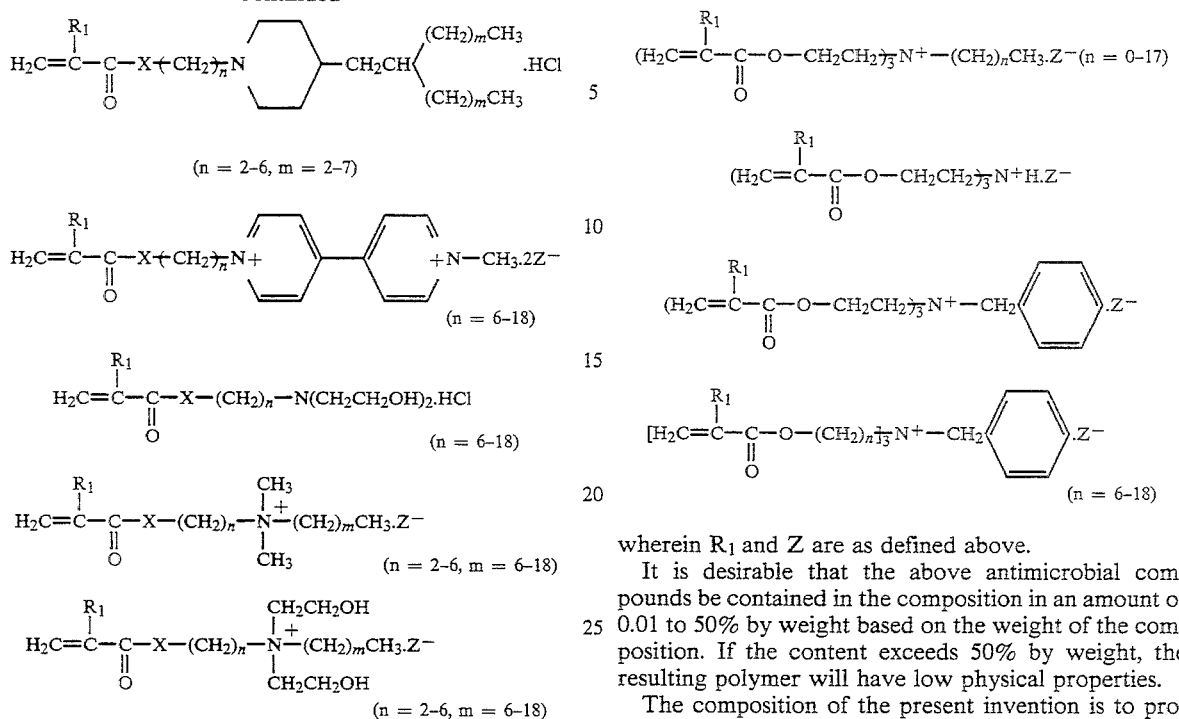

wherein $R_1$, X and Z are as defined above.
Compounds represented by formula II

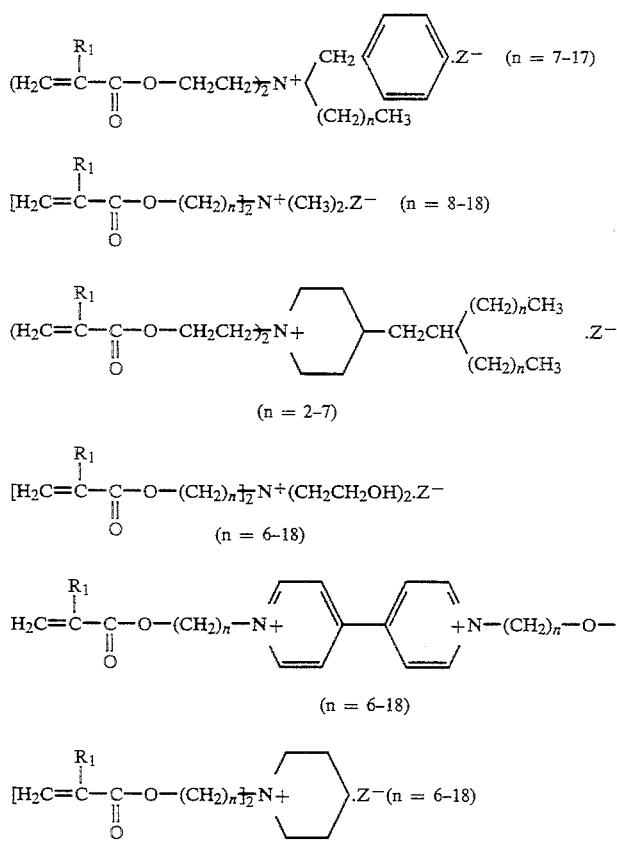

wherein $R_1$ and Z are as defined above.
Compounds represented by formula III wherein $R_1$ and Z are as defined above.

It is desirable that the above antimicrobial compounds be contained in the composition in an amount of 0.01 to 50% by weight based on the weight of the composition. If the content exceeds 50% by weight, the resulting polymer will have low physical properties.

The composition of the present invention is to produce the intended polymer, and can be supplied as it is to customers who then polymerize it upon use. Or, for those uses that require polymers, the composition can also be supplied in the form of polymers.

Linear polymers, obtained by polymerizing monofunctional monomers, are best fit for uses requiring good thermoplasticity or ready moldability. For uses requiring high hardness, thermal resistance and strength, crosslinked polymers obtained by polymerizing a monomer mixture comprising at least one multifunctional monomer are suitable. The type and amount of the multifunctional monomer may be properly selected depending on the intended use of the resulting polymer.

The polymers obtained according to the present invention have antimicrobial properties and hence they are suitably used for medical items. They are also, naturally, usable for goods for daily use and industrial purposes requiring antimicrobial properties.

Shaped articles obtained according to the present invention include membranes, films and other shapes obtained by coating or injecting the composition in a mold and then polymerizing it. They further include films, coating, fibers, hollow fibers, hollow bodies and like shapes obtained by forming the linear polymer or partially crosslinked polymers by known forming processes.

More specific uses intended by the present invention are now described. Dental applications include composite resins, adhesives, pit and fissure sealants, prosthetics, denture bases, coating materials, resins for temporary restoration, resin-based cements and artificial tooth roots. Since the surfaces of dental materials are always exposed in the dental cavity, bacteria grow thereon to a large extent. The effect of the present invention is therefore most suitably produced in the field of dental applications. Applications in orthopedics are bone cement, artificial bones, artificial joints and the like. With respect to artificial bones, the composition of the present invention is more suitably used as a coating material for them. For surgery, sutures, artificial vessels, wound-covering materials, artificial skin and the like may be mentioned. For opthalmology, soft contact lenses and hard contact lenses comprising the polymer of the present invention are suitable. In particular, the polymer is better used for soft contact lenses having high water content, which often suffer from growth of bacteria. Besides the above, the polymer of the present invention is used for disposable tubes for medical purposes, catheters and the like.

The above items may comprise, in addition to the components described above, other additives such as organic polymers, fillers, stabilizers and stains (pigments) according to the intended uses.

Important ones among these components in the present invention are next explained.

Examples of the ethylenically unsaturated monomer used in the invention are esters of an acid such as α-cyanoacrylic acid, (meth)acrylic acid, urethane(meth)acrylic acid, crotonic acid, cinnamic acid, sorbic acid, maleic acid or itaconic acid, with a mono- or dihydric alcohol; (meth)acrylamides such as N-isobutylacrylamide; vinyl esters of carboxylic acids, such as vinyl acetate; vinyl ethers such as butyl vinyl ether; mono-N-vinyl compounds such as N-vinylpyrrolidone and styrene derivatives. Particularly suitable for the purpose of the present invention are the following mono- or multifunctional (meth)acrylates and urethane(meth)acrylates. The terms (meth)acrylic acid and (meth)acrylate herein mean acrylic acid and/or methacrylic acid, and acrylate and/or methacrylate, respectively.

i) Monofunctional monomers

Methyl (meth)acrylate, n- or i-propyl (meth) acrylate, n-, i- or t-butyl (meth)acrylate, 2-hydroxyethyl (meth)acrylate, siloxanyl methacrylate and the like.

ii) Difunctional monomers

Compounds represented by the general formula

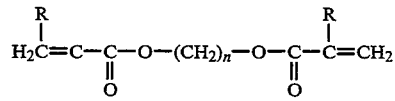

wherein n represents an integer of 3 to 20 and R represents a hydrogen atom or a methyl group.

Examples: Di(meth)acrylates of propanediol, butanediol, hexanediol, octanediol, nonanediol, decanediol, eicosanediol and the like.

Compounds represented by the general formula

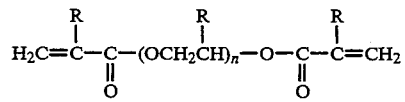

wherein n represents an integer of 1 to 14 and R represents a hydrogen atom or a methyl group.

Examples: Di(meth)acrylates of ethylene glycol, diethylene glycol, triethylene glycol, tetraethylene glycol, dodecaethylene glycol, tetradecaethylene glycol, propylene glycol, dipropylene glycol, tetradecapropylene glycol and the like; glycerine di(meth)acrylate; 2,2-bis[4-(3-methacryloyloxy-2-hydroxypropoxy)phenyl]propane ("Bis-GMA"); bisphenol-A di(meth)acrylate, neopentyl glycol di(meth)acrylate; 2,2-di(4-methacryloyloxypolyethoxyphenyl)propane (having 2 to 10 ethoxy groups in a molecule), 1,2-bis(3-methacryloyloxy-2-hydroxypropoxy)butane and the like.

iii) Tri- or more functional monomers

Trimethylolpropane tri(meth)acrylate, pentaerythritol tetra(meth)acrylate and the like.

iv) Urethane (meth)acrylate

Examples are the reaction product of 2 moles of a (meth)acrylate having a hydroxyl group and 1 mole of a diisocyanate and the reaction product urethane prepolymer having an NCO group at each of its molecular ends and a (meth)acrylate having a hydroxyl group. The products of these reactions have the following structure.

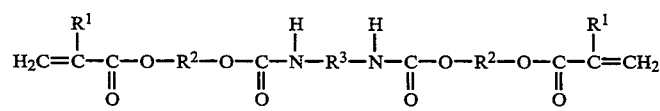

wherein $R^1$ represents a hydrogen atom or a methyl group, $R^2$ represents an alkylene group and $R^3$ represents an organic residue.

Polymerizable monomers having an acid group such as phosphoric acid group or carboxylic acid group are also usable for the purpose of the invention, and their examples are as follows.

i) Those containing a phosphoric acid group

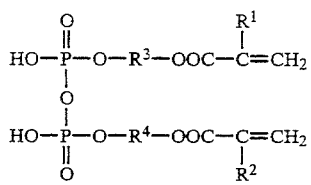

wherein $R^1$ and $R^2$ each represents a hydrogen atom or a methyl group and $R^3$ and $R^4$ each represents an organic residue.

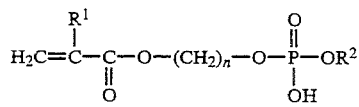

wherein $R^1$ represents a hydrogen atom or a methyl group, $R^2$ represents a hydrogen atom or a phenyl group and n represents an integer of 2 to 14.

ii) Reaction products of a (meth)acrylate having a hydroxyl group as a branch and phosphoryl chloride examples are as follows.

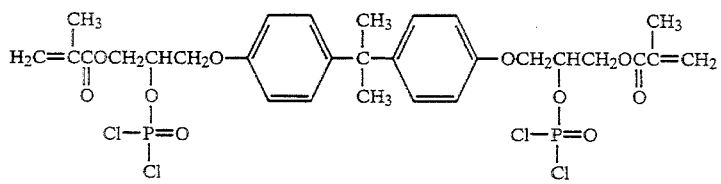

iii) Monomers having carboxyl group

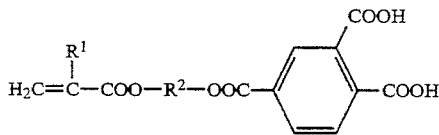

and their anhydrides

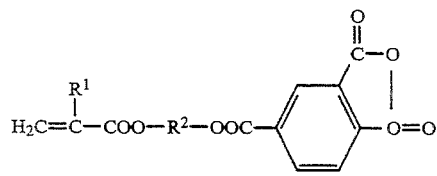

wherein $R^1$ represents a hydrogen atom or a methyl group and $R^2$ represents an organic residue. An example is 4-methacyloyloxyethyl trimellitate anhydride.

Other examples are represented by the following formula

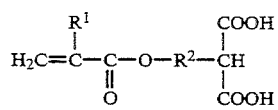

wherein $R^1$ represents a hydrogen atom or a methyl group and $R^2$ represents an organic residue. An example is

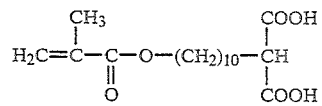

Examples of the filler which may, as required, be added to the composition of the present invention are quartz powder, alumina powder, hydroxyapatite, calcium carbonate, fluoroaluminosilicate glass, barium sulfate, titanium oxide, zirconia powder, glass powder, microfine silica and organic composite fillers containing organic components and inorganic components. Powder of polymers such as polymethyl methacrylate, polystyrene and polyvinyl chloride may also be, if necessary, added. Examples of the glass are silica glass, soda silicate glass, boro-silicated glass, barium boroaluminosilicated glass, aluminosilicate glass, strontium boroalumino-silicated glass, synthetic silica and titanium silicate glass.

It is desirable that the inorganic filler used in the present invention be surface-treated before use. Examples of surface-treating agents usable for this purpose are organosilicon compounds such as γ-methacryloxypropyltrimethoxysilane, vinyltrichlorosilane, vinyltriethoxysilane, vinyltrimethoxysilane, vinyltriacetoxysilane and vinyltri(methoxyethoxy)silane. The silane treatment is conducted in the usual manner.

Examples of the polymerization initiator used in the present invention are room-temperature initiators, e.g. peroxides such as benzoyl peroxide and cumene hydroperoxide; tributylborane; benzoyl peroxide-aromatic tertiary amine systems and aromatic sulfinic acids (or salts thereof)-aromatic secondary or tertiary amine-acyl peroxide systems. Also usable are photopolymerization initiators, e.g. camphorquinone, camphorqunone-tertiary amine systems, camphorquinone-peroxide systems, camphorquinone-aldehyde systems, camphorquinone-mercaptan systems and acylphosphine oxides. Suitably used for photopolymerization by UV irradiation are benzoin methyl ether, benzyl dimethyl ketal, benzophenone, 2-methylthioxanthone, diacetyl, benzyl, azobis-isobutyronitrile and tetramethylthiuram disulfide.

The composition of the present invention may, as required, further incorporate a polymerization inhibitor, stain, fluorescent agent, UV-absorber or like additives.

Other features of the invention will become apparent in the course of the following descriptions of exemplary embodiments which are given for illustration of the invention and are not intended to be limiting thereof.

EXAMPLES

Example 1

A dental composite resin (Composition I) was prepared by mixing 17 parts by weight of a mixture consisting of 70 parts by weight of BisGMA, 20 parts by weight of triethylene glycol dimethacrylate, 2 parts by weight of an antimicrobial component of the compound 1 shown below, 1 part by weight of camphorquinone and 2 parts by weight of dimethylaminoethyl methacrylate, and 83 parts by weight of a quartz powder surface-treated with γ-methacryloyloxypropyltrimethoxysilane and having an average particle diameter of 2.4 μm. The composition thus prepared was polymerized and formed into a disc shaped specimen having a diameter of 10 mm and a thickness of 2 mm. The specimen was sterilized with ethylene oxide gas and then evaluated for antimicrobial activity according to the evaluation methods A, A', B and B'. The results are shown in Table 1.

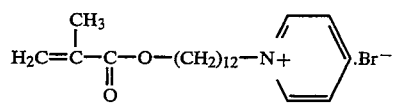

Evaluation of antimicrobial activity

Evaluation method A

On a prepared BHI (brain heart infusion) agar plate, a culture fluid of streptococcus mutans (strain MT 8184) is applied and dried. On the dried plate, a specimen having been evacuated of ethylene oxide gas is placed and incubation is conducted at 37° C. for 48 hours. After completion of the incubation, development of bacteria on the bottom surface of the specimen and that on the surrounding agar region are observed. The results are expressed in terms of the following ratings.
a) Inhibition of growth of bacteria on the surface of specimen
- −: No inhibition at all of bacterial growth beneath the surface of specimen. Bacteria have grown uniformly on the entire plate.
- ±: The effect of inhibiting bacterial growth is slightly observed on the region on the agar plate just beneath the specimen.
- +: Bacterial growth is hardly observed on the region on the agar plate just beneath the specimen.
- ++: No bacterial growth is observed at all on the region on the agar plate just beneath the specimen.
b) Development of growth-inhibition ring
- −: No inhibition ring is observed at all around the specimen.
- ±: A ring-shaped inhibition of growth is observed around the specimen, the ring having a width of less than 1 mm.
- +: A growth-inhibition ring is observed around the specimen, the ring having a width of not less than 1 mm and less than 2 mm.
- ++: A growth-inhibition ring is observed around the specimen, the ring having a width of more than 2 mm.

Evaluation method A'

The procedure of evaluation method A is followed with the specimen having been immersed in water at 37° C. for 1 month.

Evaluation method B

A specimen is hung in a $1 \times 10^7$ CFU/ml solution of streptococcus mutans and containing 1% sucrose. Incubation is conducted at 37° C. for 24 hours and then the plaque having deposited on the specimen surface is dyed and judged for the effect of inhibiting plaque deposition, of the specimen. The results are expressed in terms of the following ratings.
- −: Plaque deposition has hardly been inhibited. No difference in the amount deposited between the specimen and a control containing no antimicrobial component.
- ±: Plaque deposition has been suppressed to a certain extent.
- +: Plaque deposition has been suppressed to a considerable extent.
- ++: Almost no deposit of plaque is observed on the specimen surface Evaluation method B'

The procedure of evaluation method B is followed with the specimen having been immersed in water at 37° C. for 1 month.

Examples 2 through 6

Example 1 was repeated except that compositions containing the following compounds 2 through 6 in lieu of the compound 1 were used instead of the composition I.

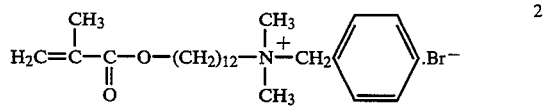

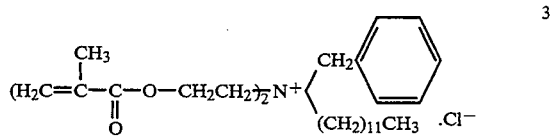

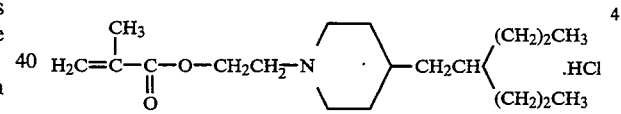

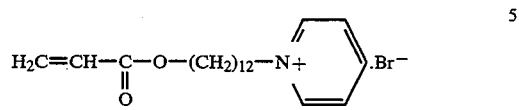

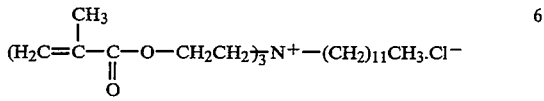

The results were all good as shown in Table 1, thus proving the fact that antimicrobial polymerizable compounds according to the present invention and other than compound 1 are also effective.

Comparative Example 1

Example 1 was repeated except that a composition that is the same as composition I but with no compound 1. The results are shown in Table 1.

Comparative Examples 2 through 5

Example 1 was repeated except that compositions containing the following compounds 7 through 10 in lieu of the compound 1 were used instead of the composition I. The results are shown in Table 1.

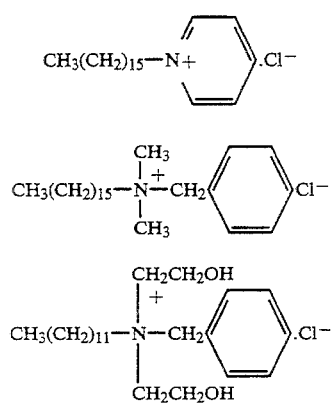

Compound 7: CH₃(CH₂)₁₅—N⁺(pyridinium).Cl⁻

Compound 8: CH₃(CH₂)₁₅—N⁺(CH₃)₂—CH₂—C₆H₅ .Cl⁻

Compound 9: CH₃(CH₂)₁₁—N⁺(CH₂CH₂OH)₂—CH₂—C₆H₅ .Cl⁻

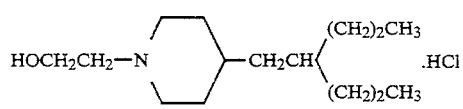

Compound 10: HOCH₂CH₂—N(piperidine)—CH₂CH((CH₂)₂CH₃)₂ .HCl

TABLE 1

| Example or Comparative Example | Antimicrobial compound | Content of antimicrobial compound (wt %) | Formation of growth-inhibition ring Method | | Inhibition of bacterial growth beneath specimen surface Method | | Suppression of plaque deposit on specimen surface Method | |
| --- | --- | --- | --- | --- | --- | --- | --- | --- |
| | | | A | A' | A | A' | B | B' |
| Example 1 | Compound 1 | 0.32 | — | — | + | + | + | + |
| Example 2 | Compound 2 | " | — | — | + | + | + | + |
| Example 3 | Compound 3 | " | — | — | ± | ± | ± | ± |
| Example 4 | Compound 4 | " | — | — | ± | ± | ± | ± |
| Example 5 | Compound 5 | " | — | — | + | + | + | + |
| Example 6 | Compound 6 | " | — | — | ± | ± | ± | ± |
| Comp. Ex. 1 | — | — | — | — | — | — | — | — |
| Comp. Ex. 2 | Compound 7 | 0.32 | ++ | — | ++ | — | ++ | — |
| Comp. Ex. 3 | Compound 8 | " | ++ | — | ++ | — | ++ | — |
| Comp. Ex. 4 | Compound 9 | " | ++ | — | ++ | — | ++ | — |
| Comp. Ex. 5 | Compound 10 | " | ++ | — | ++ | — | ++ | — |

Examples 7 through 11

Test specimens were prepared from 5 compositions comprising 5 commercial dental materials as shown in Table 2 and incorporating a designated amount of compound 1 as an antimicrobial composition. The test specimens were evaluated for antimicrobial activity according to methods A, A', B and B'. The results are shown in Table 2. The antimicrobial compound used in the present invention is also effective when used in combination with commercial dental materials.

Comparative Examples 6 through 10

Test specimens similar to those in Examples 7 through 11 were prepared by using compound 7 instead of compound 1 and evaluated in the same manner. The results are shown in Table 2.

Comparative Examples 11 through 15

Examples 7 through 11 were repeated except that the commercial dental materials were used as they were, without addition of the antimicrobial component. The results of evaluation are shown in Table 2.

TABLE 2

| Example or Comparative Example | Dental material (supplier) | Antimicrobial compound | Content of antimicrobial compound (wt %) | Formation of growth inhibition ring Method | | Inhibition of bacterial growth beneath specimen surface Method | | Suppression of plaque deposit on specimen surface Method | |
| --- | --- | --- | --- | --- | --- | --- | --- | --- | --- |
| | | | | A | A' | A | A' | B | B' |
| Example 7 | Composite resin, PHOTOCLEARFIL A (Kuraray) | Compound 1 | 0.3 | — | — | + | + | + | + |
| Example 8 | Adhesive, PANAPIA EX (Kuraray) | Compound 1 | " | — | — | ++ | + | ++ | ± |
| Example 9 | Pit & fissure sealant, TEETHMATE (Kuraray) | Compound 1 | " | — | — | ++ | + | ++ | + |
| Example 10 | Denture resin, ACRON (GC) | Compound 1 | " | — | — | + | + | + | + |
| Example 11 | Cold-curing resin, UNIFAST (GC) | Compound 1 | " | — | — | ++ | + | ++ | + |
| Comp. Ex. 6 | Composite resin, PHOTOCLEARFIL A (Kuraray) | Compound 7 | 0.3 | ++ | — | ++ | — | + | — |
| Comp. Ex. 7 | Adhesive, PANAPIA EX (Kuraray) | Compound 7 | " | ++ | — | ++ | — | ++ | — |
| Comp. Ex. 8 | Pit & fissure sealant, TEETHMATE (Kuraray) | Compound 7 | " | ++ | — | ++ | — | ++ | — |
| Comp. Ex. 9 | Denture resin, ACRON (GC) | Compound 7 | " | + | — | + | — | + | — |
| Comp. Ex. 10 | Cold-curing resin, UNIFAST (GC) | Compound 7 | " | ++ | — | ++ | — | ++ | — |
| Comp. Ex. 11 | Composite resin, PHOTOCLEARFIL A (Kuraray) | — | — | — | — | — | — | — | — |
| Comp. Ex. 12 | Adhesive, PANAPIA EX (Kuraray) | — | — | — | — | — | — | — | — |
| Comp. Ex. 13 | Pit & fissure sealant, TEETHMATE (Kuraray) | — | — | — | — | — | — | — | — |
| Comp. Ex. 14 | Denture rean, ACRON (GC) | — | — | — | — | — | — | — | — |
| Comp. Ex. 15 | Cold-curing resin, UNIFAST (GC) | — | — | — | — | — | — | — | — |

Example 12

A composition comprising 96.7 parts by weight of 2-hydroxyethyl methacrylate (HEMA), 3 parts by weight of compound 1 and 0.3 part by weight of ethylene glycol dimethacrylate was subjected to bulk polymerization with an azobis-based polymerization initiator (V-601), to give a polymer for soft contact lenses. The polymer is formed into a plate having a diameter of 70 mm and a thickness of 0.1 mm, which was then evaluated for antimicrobial activity according to the following methods.

Evaluation method C

*Paecilomyces lilacinus*, which often develops on soft contact lens, was separated, pre-incubated and prepared into a spore fluid. The spore fluid was applied onto a plate of PDA culture medium (potato, dextrose and agar). The specimen was placed on the PDA plate and incubation was then conducted at 27° C. for 7 days. After completion of the incubation, development of bacteria on and around the bottom surface of the specimen was observed. The results are expressed in terms of the following ratings.

a) Inhibition of bacteria growth on the surface of specimen

—: No inhibition at all of bacterial growth on the surface of specimen or on the agar plate just beneath the specimen.

±: The effect of inhibiting bacterial growth is slightly observed on the region on the surface of specimen and on the agar plate just beneath the specimen.

+: Bacterial growth is hardly observed on the surface of the specimen or on the agar plate just beneath the specimen.

b) Development of growth-inhibition ring

—: No inhibition of growth is observed at all around the specimen.

±: A vague growth-inhibition ring is observed around the specimen.

+: Growth-inhibition ring is clearly observed around the specimen.

Evaluation method C'

The procedure of evaluation method C is followed with the specimen having been immersed in water at 37° C. for 1 month.

The results are shown in Table 3.

Examples 13 through 17

Example 12 was repeated except that compounds 2 through 6 were used instead of compound 1. The results are shown in Table 3. Compositions containing other antimicrobial compounds and according to the present invention also give good results.

Comparative Example 16

Example 12 was repeated except that HEMA was used instead of compound 1. The evaluation results are shown in Table 3.

Comparative Examples 17 through 20

Example 12 was repeated except that compounds 7 through 10 were used instead of compound 1. The results are shown in Table 3.

TABLE 3

| Example or Comparative Example | Antimicrobial compound | Content of antimicrobial compound (wt %) | Formation of growth-inhibition ring Method | | Inhibition of bacterial growth beneath specimen surface Method | |
|---|---|---|---|---|---|---|
| | | | C | C' | C | C' |
| Example 12 | Compound 1 | 3.0 | — | — | + | + |
| Example 13 | Compound 2 | " | — | — | + | + |
| Example 14 | Compound 3 | " | — | — | ± | ± |
| Example 15 | Compound 4 | " | — | — | ± | ± |
| Example 16 | Compound 5 | " | — | — | + | + |
| Example 17 | Compound 6 | " | — | — | ± | ± |
| Comp. Ex. 16 | — | | — | — | — | — |
| Comp. Ex. 17 | Compound 7 | 3.0 | + | — | + | — |
| Comp. Ex. 18 | Compound 8 | " | + | — | + | — |
| Comp. Ex. 19 | Compound 9 | " | + | — | + | — |
| Comp. Ex. 20 | Compound 10 | " | + | — | + | — |

Example 18

Evaluation method D

*Pseudomonas aeruginosa*, which is often found in cornea infections of contact lens wearers, is separated and pre-incubated. The bacterial liquid was applied onto a plate of BHI (brain heart infusion) agar culture medium. The same specimen as in Example 12 was placed on the BHI plate and incubation was then conducted at 37° C. for 48 hours. After completion of the incubation, development of bacteria on and around the bottom surface of the specimen are observed. The results are expressed in terms of the same ratings as those for evaluation method C. The results are shown in Table 4.

Evaluation method D'

The procedure of evaluation method D is followed with the specimen having been immersed in water at 37° C. for 1 month. The results are shown in Table 4.

Example 19

Example 18 was repeated except that *Staphylococcus epidermidis* was used for evaluation instead of the *P. aeruginosa* used in Example 18. The evaluation results are shown in Table 4.

Example 20

Example 18 was repeated except that *Streptococcus pyogenes* was used for evaluation instead of *P. aeruginosa*. The evaluation results are shown in Table 4.

Comparative Examples 21 through 23

Example 18 (Example 12) was repeated except that HEMA was used instead of compound 1, to prepare a specimen. The specimen was evaluated by the same procedures as in Examples 18 through 20. The results are shown in Table 4.

Comparative Examples 24 through 26

Example 18 (Example 12) was repeated except that compound 7 was used instead of compound 1, to prepare a specimen. The specimen was evaluated by the same procedures as in Examples 18 through 20. The results are shown in Table 4.

in the same manner as in Example 20. The results are shown in Table 6.

Powder agent

TABLE 4

| Example or Comparative Example | Antimicrobial compound | Content of antimicrobial compound (wt %) | Bacterium used | Formation of growth-inhibition ring Method | | Inhibition of bacterial growth beneath specimen surface Method | |
|---|---|---|---|---|---|---|---|
| | | | | D | D' | D | D' |
| Example 12 | Compound 1 | 3.0 | P. lilacinus | — | — | + | + |
| Example 18 | Compound 1 | " | P. aeruginosa | — | — | ± | ± |
| Example 19 | Compound 1 | " | S. epidermidis | — | — | + | + |
| Example 20 | Compound 1 | " | S. pyogenes | — | — | + | + |
| Comp. Ex. 16 | — | — | P. lilacinus | — | — | — | — |
| Comp. Ex. 21 | — | — | P. aeruginosa | — | — | — | — |
| Comp. Ex. 22 | — | — | S. epidermidis | — | — | — | — |
| Comp. Ex. 23 | — | — | S. pyogenes | — | — | — | — |
| Comp. Ex. 24 | Compound 7 | 3.0 | P. aeruginosa | + | — | + | — |
| Comp. Ex. 25 | Compound 7 | " | S. epidermidis | + | — | + | — |
| Comp. Ex. 26 | Compound 7 | " | S. pyogenes | + | — | + | — |

Examples 21 through 23

A composition comprising 67 parts by weight of methyl methacrylate (MMA), 30 parts by weight of siloxanyl methacrylate and 3 parts by weight of compound 1 was subjected to bulk polymerization with an azobis-based polymerization initiator (V-601), to obtain a polymer for hard contact lenses. The polymer is formed into a plate having a diameter of 10 mm and a thickness of 0.2 mm, which was then evaluated in the same manner as in Examples 18 through 20 (evaluation method D and D'). The results are shown in Table 5.

Comparative Examples 27 through 29

Example 21 was repeated except that compound 1 was replaced by MMA, to obtain a specimen. The specimen was evaluated in the same manner as in Examples 21 through 23. The results are shown in Table 5.

Comparative Example 30 through 32

Example 21 was repeated except that compound 7 was used instead of compound 1, to obtain a specimen, which was then evaluated in the same manner as in Examples 21 through 23. The results are shown in Table 5.

Polymethyl methacrylate (PMMA): 89 parts by weight
Barium sulfate: 10
Benzoyl peroxide: 1 part by weight
Liquid agent
Methyl methacrylate (MMA): 88 parts by weight
Compound 1: 10
N,N-diethanol-p-toluidine: 2

Examples 25 through 29

Example 24 was repeated except that each of compounds 2 through 6 was used instead of compound 1. The evaluation results are shown in Table 6.

Example 30

A composition comprising 95 parts by weight of MMA and 5 parts by weight of compound 1 was emulsion-polymerized to give a particulate polymer (polymer A). The polymer thus obtained was used to prepare the following bone cement tentatively, which was evaluated in the same manner as in Example 24. The results are shown in Table 6.

Powder agent
Polymer (A): 89 parts by weight
Barium sulfate: 10

TABLE 5

| Example or Comparative Example | Antimicrobial compound | Content of antimicrobial compound (wt %) | Bacterium used | Formation of growth-inhibition ring Method | | Inhibition of bacterial growth beneath specimen surface Method | |
|---|---|---|---|---|---|---|---|
| | | | | D | D' | D | D' |
| Example 21 | Compound 1 | 3.0 | P. aeruginosa | — | — | + | + |
| Example 22 | Compound 1 | " | S. epidermidis | — | — | ± | ± |
| Example 23 | Compound 1 | " | S. pyogenes | — | — | + | + |
| Comp. Ex. 27 | — | — | P. aeruginosa | — | — | — | — |
| Comp. Ex. 28 | — | — | S. epidermidis | — | — | — | — |
| Comp. Ex. 29 | — | " | S. pyogenes | — | — | — | — |
| Comp. Ex. 30 | Compound 7 | 3.0 | P. aeruginosa | + | — | + | — |
| Comp. Ex. 31 | Compound 7 | " | S. epidermidis | + | — | + | — |
| Comp. Ex. 32 | Compound 7 | " | S. pyogenes | + | — | + | — |

Example 24

A bone cement comprising the following powder agent and liquid agent was tentatively prepared. The powder agent and the liquid agent were mixed in a ratio of 2/1 (g/ml) and the mixture was put into a split mold having a diameter and thickness of 10 mm and 3 mm, respectively, and cured therein. The cured article was allowed to stand at 37° C. for 1 day and then evaluated Benzoyl peroxide: 1 part by weight
Liquid agent
MMA: 98 parts by weight
N,N-diethanol-p-toluidine: 2

Examples 31 through 33

Example 30 was repeated except that each of compounds 2, 4 and 5 was used instead of compound 1. The evaluation results are shown in Table 6.

Comparative Example 33

Example 24 was repeated except that compound 1 in the liquid agent was replaced by MMA. The evaluation results are shown in Table 6.

Comparative Examples 34 through 37

Example 24 was repeated except that compound 1 in the liquid agent was replaced by each of compounds 7 through 10. The evaluation results are shown in Table 6.

Examples 37 through 41

Example 34 was repeated except that compounds 2 through 6 were each used instead of compound 1. The evaluation results are shown in Table 7.

Comparative Example 7

Example 34 was repeated except that the collagen nonwoven fabric was used as it was. The results are shown in Table 7.

TABLE 7

| Example or Comparative Example | Antimicrobial compound | Bacterium used | Formation of growth-inhibition ring Method | | Inhibition of bacterial surface Method | |
|---|---|---|---|---|---|---|
| | | | D | D' | D | D' |
| Example 34 | Compound 1 | P. aeruginosa | — | — | + | + |
| Example 35 | Compound 1 | S. epidermidis | — | — | ± | ± |
| Example 36 | Compound 1 | S. pyogenes | — | — | + | + |
| Example 37 | Compound 2 | P. aeruginosa | — | — | + | + |
| Example 38 | Compound 3 | P. aeruginosa | — | — | + | + |
| Example 39 | Compound 4 | P. aeruginosa | — | — | ± | ± |
| Example 40 | Compound 5 | P. aeruginosa | — | — | + | + |
| Example 41 | Compound 6 | P. aeruginosa | — | — | ± | ± |
| Comp. Ex. 38 | — | P. aeruginosa | — | — | — | — |

Example 42

A composition comprising 80 parts by weight of methyl methacrylate (MMA) and 20 parts by weight of compound 1 was subjected to bulk polymerization with an azobis-based polymerization initiator (V-601), to

TABLE 6

| Example or Comparative Example | Antimicrobial compound | Content antimicrobial compound (wt %) | Formation of growth-inhibition ring Method | | Inhibition of bacterial growth beneath specimen surface Method | |
|---|---|---|---|---|---|---|
| | | | C | C' | C | C' |
| Example 24 | Compound 1 | about 3.0 | — | — | + | + |
| Example 25 | Compound 2 | " | ± | — | + | + |
| Example 26 | Compound 3 | " | — | — | + | + |
| Example 27 | Compound 4 | " | ± | — | ± | ± |
| Example 28 | Compound 5 | " | — | — | + | + |
| Example 29 | Compound 6 | " | — | — | + | + |
| Example 30 | Compound 1 | " | — | — | + | + |
| Example 31 | Compound 2 | " | — | — | + | + |
| Example 32 | Compound 4 | " | — | — | + | + |
| Example 33 | Compound 5 | " | — | — | + | + |
| Comp. Ex. 33 | — | — | — | — | — | — |
| Comp. Ex. 34 | Compound 7 | about 3.0 | + | — | + | — |
| Comp. Ex. 35 | Compound 8 | " | + | — | + | — |
| Comp. Ex. 36 | Compound 9 | " | + | — | + | — |
| Comp. Ex. 37 | Compound 10 | " | + | — | + | — |

Examples 34 through 36

In 100 ml of water was dissolved 5 g of compound 1. In the obtained solution 5 g of a collagen nonwoven fabric was immersed. To the mixture, 2.5 ml of 1N nitric acid containing 0.1 mole/l of ammonium-cerium nitrate was added, and polymerization was effected at 20° C. under an atmosphere of nitrogen for 10 hours. The nonwoven fabric thus treated was repeatedly washed with water and acetone, to give a wound-covering material (artificial skin) comprising a collagen nonwoven fabric to which compound 1 has been graft-polymerized. The material thus obtained was cut to square sheets of 10×10 mm, which were then evaluated for antimicrobial activities in the same manner as in Examples 18 through 20 (by evaluation methods D and D'). The results are shown in Table 7.

give a polymer having a number average polymerization degree of about 50,000. To remove residual monomers, the polymer obtained was dissolved in methylene chloride, and reprecipitated from hexane and collected by filtration. The thus purified polymer was named polymer-B. A 5% by weight solution of the polymer-B in methylene chloride was prepared. A polyvinyl chloride catheter was immersed in the thus prepared solution. The catheter was then taken out and the adhering methylene chloride was sufficiently evaporated off, to give a catheter surface-coated with polymer-B. The thus surface-treated catheter and an untreated catheter were compared for antimicrobial activities according to the following method.

Evaluation method E

*Staphylococcus epidermidis* is separated and pre-incubated. The bacteria liquid is inoculated on a BHI culture medium. A specimen is immersed in the thus prepared liquid culture medium and aerobic incubation is conducted at 37° C. for 48 hours. The specimen is taken out and gram stained. The condition of bacterial growth on the specimen surface is observed and judged according to the following ratings.

- —: No inhibition at all of bacterial growth on the surface of the specimen (bacteria have grown to the same extent as or even larger extent than on the surface of the untreated specimen).
- ±: The effect of inhibiting bacterial growth is slightly observed on the surface of specimen, i.e. bacteria have grown to a smaller extent than with the untreated specimen.
- +: Bacterial growth is hardly observed on the surface of the specimen.

The results of evaluation are shown in Table 8.

Examples 43 through 45

Example 42 was repeated except that a suture (made of silk), an artificial skin (made of formalized polyvinyl alcohol) or an artificial vessel (made of segmented polyurethane) was used instead of the catheter used in Example 42. The evaluation results are shown in Table 8.

Comparative Examples 39 through 42

Examples 42 through 45 were repeated except that PMMA (polymethyl methacrylate) was used instead of polymer-B. The results are shown in Table 8.

TABLE 8

| Example or Comparative Example | Antimicrobial compound | Content of antimicrobial compound (wt %) | Inhibition of bacterial growth on specimen surface Evaluation method E |
|---|---|---|---|
| Example 42 | Compound 1 | 20 | + |
| Example 43 | Compound 1 | " | + |
| Example 44 | Compound 1 | " | + |
| Example 45 | Compound 1 | " | ± |
| Comp. Ex. 39 | — | — | — |
| Comp. Ex. 40 | — | — | — |
| Comp. Ex. 41 | — | — | — |
| Comp. Ex. 42 | — | — | — |

Obviously, numerous modifications and variations of the present invention are possible in light of the above teachings. It is therefore to be understood that within the scope of the appended claims, the invention may be practiced otherwise than as specifically described herein.

What is claimed is:

1. A polymerizable composition comprising an ethylenically unsaturated monomer and a monomer in an amount of 0.01 to 50% by weight of the following formula having antimicrobial activity and a polymerization initiator

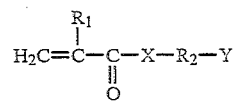

wherein $R_1$ represents a hydrogen atom or a methyl group, $R_2$ represents an alkylene group having 6 to 18 carbon atoms, X represents an oxygen atom, a sulfur atom or an imide group, Y represents:

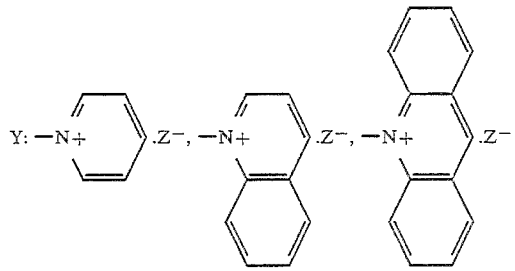

and $Z^-$ represents a chloride or a bromide.

* * * * *

UNITED STATES PATENT AND TRADEMARK OFFICE
CERTIFICATE OF CORRECTION

PATENT NO. : 5,408,022
DATED : April 18, 1995
INVENTOR(S) : Satoshi Imazato, et. al.

It is certified that error appears in the above-indentified patent and that said Letters Patent is hereby corrected as shown below:

Column 1, line 26, delete "then" and insert -- them --.

Column 4, line 20, in the formula, delete "(n=0-18)" and insert --(n=6-18)--.

Column 13, Table 2, Comp. Ex. 14, delete "rean" and insert --resin--.

Column 15, line 1, delete "70 mm" and insert --10 mm--.

Signed and Sealed this

Seventh Day of May, 1996

Attest:

BRUCE LEHMAN

*Attesting Officer*   Commissioner of Patents and Trademarks